United States Patent [19]
Gallo et al.

[11] Patent Number: 5,654,273
[45] Date of Patent: Aug. 5, 1997

[54] SYNDUCIN MEDIATED MODULATION OF TISSUE REPAIR

[75] Inventors: Richard L. Gallo, Natick; Merton Bernfield, Boston, both of Mass.

[73] Assignee: Children's Medical Center Corporation, Boston, Mass.

[21] Appl. No.: 310,722

[22] Filed: Sep. 22, 1994

[51] Int. Cl.$^6$ .................. A61K 38/00; C07K 5/00; C07K 7/00; C07K 17/00
[52] U.S. Cl. ................. 514/12; 514/8; 530/324
[58] Field of Search ............ 514/12, 8; 530/324

[56] References Cited

U.S. PATENT DOCUMENTS

| | | | |
|---|---|---|---|
| 3,625,214 | 12/1971 | Higuchi | 128/260 |
| 4,244,946 | 1/1981 | Rivier et al. | 424/177 |
| 4,305,872 | 12/1981 | Johnston et al. | |
| 4,316,891 | 2/1982 | Guillemin et al. | 424/177 |
| 4,629,784 | 12/1986 | Stammer | 530/328 |
| 4,789,734 | 12/1988 | Pierschbacher | 530/395 |
| 4,792,525 | 12/1988 | Ruoslahti et al. | 435/240.243 |
| 4,906,474 | 3/1990 | Langer et al. | 424/428 |
| 4,925,673 | 5/1990 | Steiner et al. | 424/455 |
| 4,946,830 | 8/1990 | Pulverer et al. | 514/23 |
| 5,004,735 | 4/1991 | Okamato et al. | 514/134 |

FOREIGN PATENT DOCUMENTS

WO92/22578  12/1992  WIPO.

OTHER PUBLICATIONS

Bernfield et al., Ann. Rev. Cell Biol., (1992) 8, 365–393.
Patel, Biochem. Soc. Tram., (1989), 17(5), pp. 931.
McMartin, Biochem. Soc. Trans., (1989), 17(5) pp. 931–934.
Bundgard et al., Biochem. Soc. Trans. (1989) 17(5) pp. 947–949.
Bernfield et al., Development (1993) Suppl. pp. 205–212.
Agerberth Birgitta, et al., "Amino acid sequence of PR–39—Isolation from pig intestine of a new member of the family of proline–arginine–rich antibacterial peptides," *Eur. J. of Biochem.* 202(3):849–854 (1991).
Bernfield, M., *J. Cell. Biochem.* Suppl. 17 part E. (1993).
Breuing, K.L., et al., "Healing of Partial Thickness Porcine Skin Wounds in a Liquid Environment," *J. Surg. Res.*, 52:50 (1992).
Couchman, John R. and Magnus Hook, "Proteoglycans and Wound Repair,"*The Molecular and Cellular Biology of Wound Repair*, Clark and Henson, Editors, Plenum Press, New York and London, Chapter 19:437–470 (1988).
Elenius, Klaus, et al., "Induced Expression of Syndecan in Healing Wounds," *J. Cell. Biol.*, 114:585 (1991).
Elenius, Klaus, et al., "Binding of Human Syndecan to Extracellular Matrix Proteins," *J. Biol. Chem.* 265:17837–17843 (1990).
Elenius, Klaus, et al., "Growth Factors Induce 3T3 Cells to Express bFGF-binding Syndecan," *J. Biol Chem.* 267:6435–6441 (1992).

Gallo, Richard L. et al., "Syndecans, cell surface heparan sulfate proteoglycans, are induced by a proline–rich antimicrobial peptide from wounds," *Proc. Natl. Acad. Sci. USA* 91:11035–11039 (1994). Oral presentation at the American Society of Cell Biology Annual Meeting on Dec. 14, 1994.
Gregoriadis, Gregory, Chapter 14. "Liposomes", *Drug Carriers in Biology and Medicine* pp. 287–341 (Academic Press, 1979).
Guan, Jun–Lin, et al., "Fibronectin/integrin interaction induces tyrosince phosphoylation of a 120–kDa protein," *Cell Reg.*, 2:951 (1991).
Guido, David, "Integral membrane heparan sulfate proteoglycans," *FASEB J.*, 7:1023 (1993).
Guido, David, et al., "Molecular Cloning of a Phosphatidylinositol–anchored Membrane Heparan Sulfate Proteoglycan from Human Lung Fibroblasts," *J. Cell. Biol.*, 111:3165 (1990).
Hayashi, Kimiko, et al., "Immunocytochemistry of Cell Surface Heparan Sulfate Proteoglycan in Mouse Tissues. A Light and Electron Microscopic Study," *J. Histochem. Cytochem.*, 35:1079 (1987).
Higashiyama, Shigeki, et al., "Heparin–binding EGF–like Growth Factor Stimulation of Smooth Muscle Cell Migration: Dependence of Interactions with Cell Surface," *J. Cell Bio.*, 122:933–940 (1993).
Inki, Pirio, et al., "Expression of syndecan–1 induced by differentiation and suppressed by malignant transformation of human keratinocytes," *Eur. J. Cell Bio.*, 63(1):43–51 (1994).
Jalkanen, Markku, et al., "Syndecan: Regulator of Cell Morphology and Growth Factor Action at the Cell–matrix Interface," *Trends Glycosci. Glycotechnol.* 5(22):107–120 (1993).
Jalkanen, Markku, et al., "Heparan Sulfate Proteoglycans from Mouse Mammary Epithelial Cells: Localization on the Cell Surface with a Monoclonal Antibody," *J. Cell. Biol.*, 101:976 (1985).

(List continued on next page.)

*Primary Examiner*—Avis M. Davenport
*Attorney, Agent, or Firm*—Arnall Golden & Gregory

[57] ABSTRACT

The membrane permeating antibacterial peptide, PR-39, previously found only in the intestine, was purified from wound fluid and shown to possess syndecan-1 and syndecan-4 inductive activity specifically in mesenchymal cells. This is a newly recognized function that defines peptide containing syndecan-inducing activity, and that are known as synducins. Therefore a molecule with both antimicrobial and synducin activities is deposited in wounds where it can simultaneously reduce infection and influence the action of growth factors, matrix components, and other cellular effectors involved in wound repair. Synducins, including PR-39, and derivatives thereof, is therefore useful in the modulation of wound healing, as well as other disorders involving mesenchymal cells and cell surface molecular interaction, including metastatic disease, angiogenesis, restenosis, stasis or decubitis ulcers, and prevention of keloids.

9 Claims, 3 Drawing Sheets

OTHER PUBLICATIONS

Jalkanen, Markku, et al., "Syndecan—A Cell Surface Proteoglycan That Selectively Binds Extracellular Effector Molecules," *Adv. Exp. Med. Biol.* 313, 79–85 (1992), Edited by D.A. Lane, et al., Plenum Press, New York.

McGee, Gregory S., et al., "Recombinant Basic Fibroblast Growth Factor Accelerates Wound Healing," *J. Surg. Res.* 45:145–153 (1988).

Merrifield, R.B., "Solid Phase Peptide Synthesis. I. The Synthesis of a Tetrapeptide," *J. Am. Chem. Soc.* 85, 2149 (1963).

Rapraeger, Alan C., et al., "Requirement of Heparan Sulfate for bFGF–Mediated Fibroblast Growth and Myoblast Differntiation," *Science*, 252:1705 (1991).

Rapraeger, Alan C., "The coordinated regulation of heparan sulfate, syndecans and cell behavior," *Curr. Opin. Cell Biol.*, 5:844 (1993).

Rosenberg, Rorbert D. and Paul S. Damus, "The Purification and Mechanism of Action of Human Antithrombin–Heparin Cofactor," *J. Biol. Chem.* 248:6490–6505 (1973).

Ruoslahti, Erkki and Yu Yamaguchi, "Proteoglycans as Modulators of Growth Factor Activities," *Cell*, 64:867 (1991).

Salmivirta, Markku, et al., "Basic Fibroblast Growth Factor–Syndecan Complex at Cell Surface or Immobilized to Matrix Promotes Cell Growth," *J. Biol. Chem.* 267(25):17606–17610 (1992).

Sanderson, Ralph D., et al., "Fine Structure of Heparan Sulfate Regulates Syndecan-1 Function and Cell Behavior," *J. Biol. Chem.* 269(18):13100–13106 (1994).

Saunders, Scott and Merton Bernfield, "cell Surface Proteoglycan Binds Mouse Mammory Epithelial Cells to Fibronectin and Behaves as a Receptor for Interstitial Matrix," *J. Cell. Biol.* 106:423–430 (1988).

Shi, Jishu, et al., "Identification of a proline–arginine–rich antibacterial peptide from neutrophils that is analogous to PR–39, an antibacterial peptide from the small intestine," *J. Leukocyte Biol.* 56:807–811 (1994).

Trautman, Michael S., et al., "Developmental expression of syndecan, an integral membrane proteoglycan, correlates with cell differentiation," *Development*, 111:213 (1991).

Vainio, Seppo and Irma Thesleff, "Coordinated Induction of Cell Proliferation and Syndecan Expression in Dental Mesenchyme by Epithelium: Evidence for Diffusible Signals," *Dev. Dynamics* 194:105–117 (1992).

Woods, Anne, et al., "A synthetic Peptide from the COOH–Terminal Heparin–binding Domain of FIbronectin Promotes Focal Adhesion Formation," *Molec. Biol. Cell*, 4:605 (1993).

Yayon, Ayner, et al., "Cell Surface, Heparin–like Molecules Are Required for Binding of Basic Fibroblast Growth Factor to Its High Affinity Receptor," *Cell*, 64:841 (1991).

McGee et al., *Journal of Surgical Research*, vol. 45, pp. 145–153, 1988.

Salmivirta et al, *J. Biological Chemistry*, vol. 267, No. 25, Sep. 5, 1992, pp. 17606–17610.

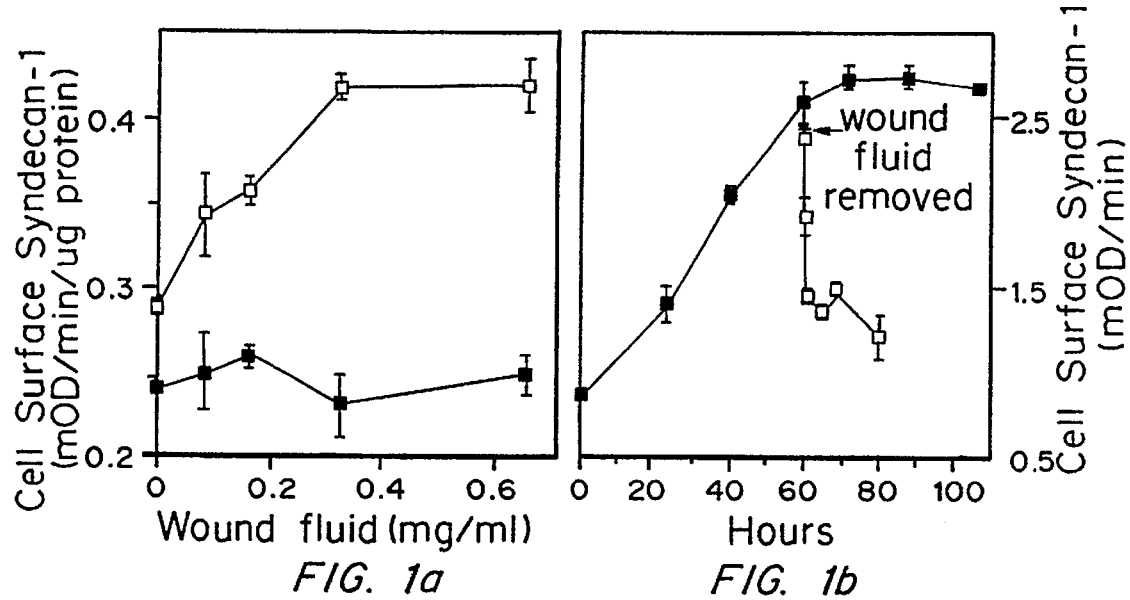
FIG. 1a
FIG. 1b
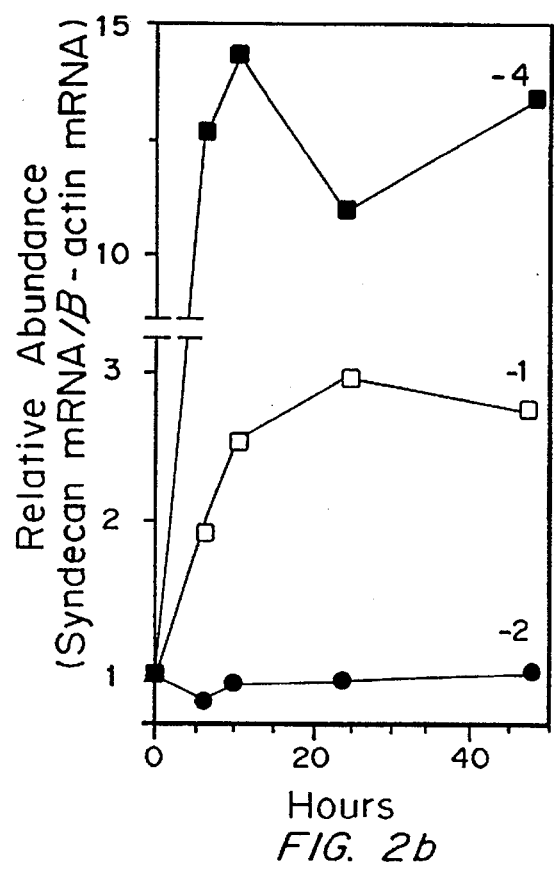
FIG. 2b

SYNDUCIN MEDIATED MODULATION OF TISSUE REPAIR

The United States government has rights in this invention by virtue of National Institutes of Health grants K08AR01874 to Richard Gallo and R01 CA28735, R37 HD06763 and P30 HL46491 to Merton Bernfield.

BACKGROUND OF THE INVENTION

This invention is generally in the area of modulation wound repair using a peptide inducer of syndecan expression.

Complex cellular behaviors such as those resulting in wound repair are influenced by a variety of soluble growth factors, cytokines, and insoluble extracellular matrix components. To exert their effects, many of these effector molecules must bind to the heparan sulfate chains that are at the surface of nearly all adherent cells (Ruoslahti and Yamaguchi, Cell, 64:867 (1991)). For example, interaction with cell surface heparan sulfate is required for cells to respond to the growth factors FGF-2 (Rapraeger, et al., Science, 252:1705 (1991); Yayon, et al. Cell, 64:841 (1991)) and HB-EGF (Higashiyama, et al., J. Cell Bio., 122:933–940 (1993)), and to the matrix component fibronectin (Guan, et al. Cell Reg., 2:951 (1991); Woods, et al., Molec. Biol. Cell, 4:605 (1993)). Indeed, Guan, et al. (1991); Bernfield, et al., in Annu. Rev. Cell Biol., G. E. Palade, B. M. Alberts, J. A. Spudich, Eds. (Annual Reviews Inc., Palo Alto, Calif., 1992), 8:365–393); Jalkanen, et al., Trends in Glyco-science and Glycotech, 5:107 (1993); G. David, FASEB J., 7:0123 (1993); and A. C. Rapraeger, Curr. Opin. Cell Biol., 5:844 (1993)) have proposed that cell surface heparan sulfate, which is derived mostly from the four members of the syndecan family of transmembrane proteoglycans (G. David, et al., J. Cell Biol., 111:3165 (1990)), acts together with specific signaling receptors to mediate the cellular response to such effectors. Changes in the abundance of cell surface heparan sulfate probably regulates the action of these effector molecules, yet it is not known how the amount of heparan sulfate at the cell surface is controlled.

Cell surface heparan sulfate mediates the activity of several growth factors, extracellular matrix components, proteases and other cellular effectors involved in wound repair. Syndecan-1, a major transmembrane heparan sulfate proteoglycan, is induced transiently on mesenchymal cells during the repair of skin wounds. Accordingly, induction of syndecan-1 can influence this process. Syndecan-1 induction can trigger cellular behaviors such as proliferation and migration that are involved in wound repair due to its ability to bind and thus augment the action of heparin-binding growth factors, including FGF-2, HB-EGF, and PDGF-AB, each found in repairing wounds. Cell surface syndecan-1 can also bind fibronectin, thrombospondin, tenascin and the fibrillar collagens. Accordingly, its induction can contribute to the effects of these extracellular matrix components that are involved in wound repair. Thus, the induction of syndecan-1 by PR-39 may mediate growth factor responsiveness and the changes in cell proliferation, migration, and adhesion that must take place for wound repair to proceed.

The expression of syndecan-1 is highly regulated in vivo. In mature tissues, syndecan-1 is expressed on the surface of epithelial cells but not on the surface of mesenchymal cells (K. Hayashi, et al., J. Histochem. Cytochem., 35:1079 (1987)). However, during cutaneous wound repair in the mouse, syndecan-1 is lost from the surface of the epithelial cells migrating into the wound and is induced on the dermal endothelial cells and fibroblasts of the forming granulation tissue (K. Elenius, et al., J. Cell Biol., 114:585 (1991)). These changes resemble those occurring during embryonic tissue interactions: syndecan-1 is lost from epithelia undergoing changes in shape while it is induced on their associated mesenchymal cells (Trautman, et al., Development, 111:213 (1991)). Thus, in both wound repair and morphogenesis, situations that correspond with changes in expression of several potential ligands, including growth factors, matrix components, proteases and protease inhibitors, mesenchymal cells are induced to increase syndecan-1 at their surfaces.

It is therefore an object of the present invention to provide a method and means for modulating tissue repair and other cellular processes involving heparan sulfate binding to ligands through inducement of syndecan expression.

It is a further object of the present invention to provide methods and composition for modulating wound repair and healing in a cell specific manner.

SUMMARY OF THE INVENTION

An activity that induces syndecan expression (synducin) was found to be present in the fluid derived from skin wounds only during the early phase of wound repair, but not in several other biological fluids or with several growth factors and cytokines. Induction of cell surface syndecans is restricted to confluent cells of mesenchymal origin and is accompanied by increased syndecan-1 and -4 mRNA levels, stability at the cell surface and reduced glycosylation. The membrane permeating antibacterial peptide, PR-39, previously found only in the intestine, was purified from wound fluid and shown to possess this inductive activity. This newly recognized function for an antimicrobial peptide indicates that a molecule with both antimicrobial and syndecan inductive activities is deposited in wounds where it can simultaneously reduce infection and influence the action of growth factors, matrix components, and other cellular effectors involved in tissue repair.

Synducins, including PR-39, and derivatives thereof, are therefore useful in the modulation of wound healing, as well as other disorders involving mesenchymal cells and ligand interactions with cell surface heparan sulfate, including metastatic disease, angiogenesis, restenosis, stasis or decubitis ulcers, and prevention of keloids.

BRIEF DESCRIPTION OF THE DRAWINGS

FIG. 1A is a graph of cell surface syndecan-1 (mOD/min/µg protein) as a function of wound fluid preparation concentration (mg/ml) showing that induction of cell surface syndecan-1 is dependent on wound fluid concentration and cell density, for post-confluent (open squares) or 50% confluent (closed circles) NIH 3T3 cells.

FIG. 1B is a graph of cell surface syndecan-1 (mOD/min) over time (hours) showing that wound fluid stabilizes induced syndecan-1 at the cell surface of post-confluent NIH 3T3 cells. Post-confluent NIH 3T3 cells were cultured in medium containing the wound fluid preparation (400 µg protein/ml), for the time periods indicated (20, 40, 60, 80, and 100 hrs) and then assayed by ELISA. At 60 hours some wells (open squares) were rinsed once with medium and fresh medium without wound fluid added prior to assay.

FIGS. 2A and 2B show syndecan mRNA levels in NIH-3T3 cells as a function of time after culture with the wound fluid preparation (400 µg/ml) showing that syndecan-1 and -4 are specifically induced.

DETAILED DESCRIPTION OF THE INVENTION

Figure 2A:
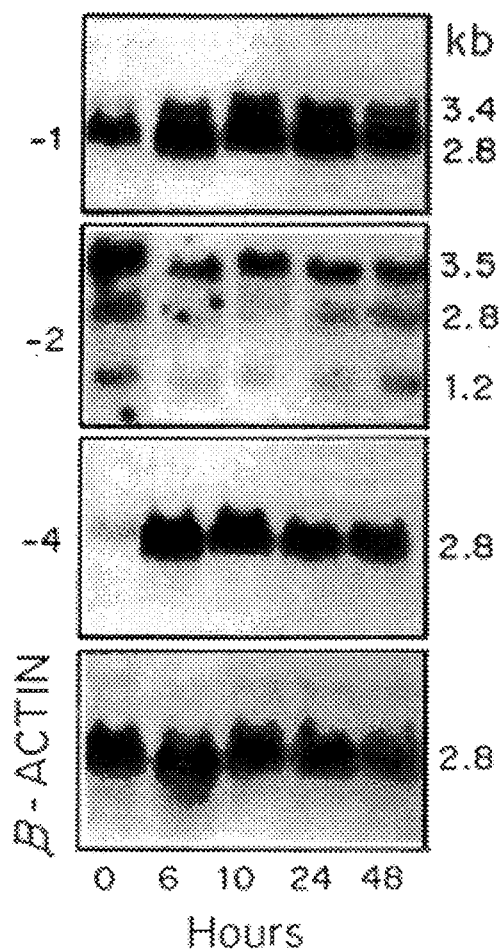

It has been discovered that a 39 amino acid peptide, PR-39, and biologically active derivatives thereof, induces syndecan-1 and -4 expression in mesenchymal cells. Methods for formulating pharmaceutical compositions and uses thereof in modulating the tissue healing response and management of various disorders and diseases based on this discovery have been developed.

Synducin

PR-39 is the 39 amino acid sequence shown in Sequence ID No. 1, Arg Arg Arg Pro Arg Pro Pro Tyr Leu Pro Arg Pro Arg Pro Pro Phe Phe Pro Pro Arg Leu Pro Pro Arg Ile Pro Pro Gly Phe Pro Pro Arg Phe Pro Pro Arg Phe Pro. The specific peptide can be substituted using conservative substitutions of amino acids having the same or functionally equivalent charge and structure, except for the amino acid sequence Arg Arg Arg at the N-terminus and the amino acid sequences Pro Pro X X Pro Pro X X Pro and Pro Pro X X X Pro Pro X X Pro, where X is any amino acid. Although described with reference to the 39 amino acid sequence, the peptide could be part of a fusion protein, immobilized to an inert substrate, or targeted using a specific ligand, or a part of a longer protein. These peptides are collectively referred to herein as "synducin" and are characterized by the biological activity further described in the following examples: specific inducement of syndecan-1 and syndecan-4 expression on the surface of mesenchymal cells, specific inducement of syndecan-1 and syndecan-4 mRNA within the cells, increase in level of cell surface heparan sulfate, and rapid uptake into mesenchymal cells to a saturation level.

Peptides are currently used as pharmaceuticals. These can be stabilized to extend half-lives in vivo by chemical modification of the amino acids or by attachment to a carrier molecule or inert substrate. For example, the peptide can be conjugated to a carrier protein such as albumin by its N-terminal cysteine by standard procedures such as the commercial Imject kit from Pierce Chemicals or expressed as a fusion protein, which may have increased efficacy. Alternatively, peptides containing cyclopropyl amino acids, or amino acids derivatized in a similar fashion, can also be used. These peptides retain their original activity but have increased half-lives in vivo. Methods for modifying amino acids, and their use, are known to those skilled in the art, for example, as described in U.S. Pat. No. 4,629,784 to Stammer.

The synducin peptide can be synthesized using standard amino acid synthetic techniques. An example is the solid phase synthesis described by J. Merrifield, 1964 J. Am. Chem. Soc. 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891, the teachings of which are incorporated herein. These methods can be used to synthesize peptides having identical sequence to the receptor proteins described herein, or substitutions or additions of amino acids, which can be screened for activity as described above.

PR-39 can also be obtained from Magainin, Inc. of Plymouth Meeting, Pa.

Pharmaceutical Preparations

The synducin can be administered systemically, topically, or locally. The peptide can be administered as the peptide or as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature.

The compounds can be administered topically by application of a solution, cream, gel, or polymeric material (for example, a Pluronic™, BASF).

Alternatively, the compound can be administered in liposomes or microspheres (or microparticles), which can be injected for local or systemic delivery. Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", Drug Carriers in Biology and Medicine pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

Based on the following in vitro studies, an effective concentration of peptide is between 0.1 and 1.0 micromolar for systemic administration and between 0.2 and 5.0 micromolar for topical administration. These ranges are well within the effective concentrations for the in vivo administration of peptides, based on comparison with the RGD-containing peptides, described, for example, in U.S. Pat. No. 4,792,525 to Ruoslahti, et al., used in vivo to alter cell attachment and phagocytosis.

Clinical Applications

Synducin induces the expression of syndecan-1 and syndecan-4 on the surface of mesenchymal cells, especially fibroblasts and endothelial cells. The syndecans are a family of heparan sulfate proteoglycans that are present on the surface of cells. The amount and type of cell surface syndecan is specifically regulated during development and wound repair. Cells require this heparan sulfate in order to respond to components in their environment such as growth factors, extracellular matrix molecules, proteases and protease inhibitors. Thus the amount and type of syndecan at the cell surface appears to determine the behavioral response of cells in their environment.

The molecules that interact with the syndecans have known in vivo effects: basic fibroblast growth factor (bFGF) accelerates wound repair and angiogenesis, as reported by McGee, et al., *J. Surg. Res.* 45, 145–153 (1988) and Salmivirta, et al., *J. Biol. Chem.* 267(25), 17606–17610 (1992); platelet derived growth factor (PDGF) induces vascular restenosis and angiogenesis; and vascular endothelial growth factor (VEGF) induces angiogenesis. Extracellular matrix components have similarly known effects: both fibronectin fragments and laminin fragments are antimetastatic and are known to bind syndecans, as described by Saunders and Bernfield, *J. Cell. Biol.* 106:423–430 (1988); Elenius, et al. *J. Biol. Chem.* 265:17837–17843 (1990). Protease inhibitors such as antithrombin III are known anticoagulants that require heparin or heparan sulfate for activity, as described by Rosenberg, R. D. and Damus P. S., *J. Biol. Chem.* 248:6490–6505 (1973).

Accordingly, clinical applications in which administration of synducin is beneficial include the treatment of stasis ulcers, for example, resulting from diabetes, and decubitus ulcers, as from chronic pressure in bedridden patients, preventing keloids in repairing wounds or treating keloids directly, all by promoting fibroblast and connective tissue growth; treatment of skin burns by accelerating re-epithelization; treating ischemic tissues, including hearts following coronary occlusion and limbs after vascular blockade, by promoting neovascularization; preventing metastases of carcinomas by augmenting the connective tissue response; direct treatment of sarcomatous growth and metastasis; treatment of hypercoagulation states, including disseminated intravascular coagulation following sepsis. Further support for the role of increasing syndecan-1 expression is found by reference to the literature relating to syndecan-1. For example, Sanderson, et al., *J. Biol. Chem.* 269(18), 13100–13106 (1994) reports on how the fine structure of heparan sulfate regulates syndecan-1 function and cell behavior; Jalkanen, et al., *Trends Glycosci. Glycotechnol.* 5(22), 107–120 (1993) and *Adv. Exp. Med. Biol.* 313, 79–85 (1992) report that syndecan selectively binds extracellular effector molecules and regulates cell morphology and growth factor action at the cell-matrix interface; Bernfield, *J. Cell. Biochem. Suppl.* 17 part E, (1993) reviews the role of the syndecans as co-receptors for matrix and growth factors in development and wound repair; Inki, et al., *Eur. J. Cell Biol.* 63(1), 43–51 (1994), reports that malignant transformation of keratinocytes is associated with a marked reduction of syndecan-1 expression in squamous cell carcinomas.

Synducin administration will be determined using the judgment of the attending physician and the type of disorder. For example, if the condition occurs locally, sufficient synducin to achieve the desired effect locally will be administered. If the condition is systemic, for example, prevention of metastases or treatment of ischemic damage, then the synducin is administered systemically. The synducin will typically be administered alone or in combination with other molecules that are regulated by binding to cell surface syndecans, such as FGF-2, PDGF, VEGF, and HB-EGF.

In an alternative embodiment, endogenous synducin can be inhibited from inducing syndecan expression. This can be effectively achieved using an inhibitor of synducin activity, an antibody against synducin, or an inhibitor of synducin expression. Inhibitors can be peptides which penetrate into cells to compete with the effect of endogenous synducin (as determined using the assays in the examples below), antisense binding to the gene expressing the endogenous synducin, and organic molecules which would inhibit expression. Antisense can be made using conventional techniques based on the codons known to encode the amino acids forming the synducin amino acid sequence.

The present invention will be further understood by reference to the following non-limiting examples.

EXAMPLE 1

Determination that cell surface syndecan-1 is induced by a component of wound fluid An in vitro cell culture system was used to explore the mechanism by which cell surface syndecans is induced. NIH 3T3 cells grown to confluence in serum-containing medium were exposed to potential inducers and then evaluated by ELISA for the amount of cell surface syndecan-1.

Syndecan-1 at the cell surface was determined on cells cultured in 96 well tissue culture plates by washing the cells once in Tris buffered saline (TBS) (10 mM Tris, 150 mM NaCl, pH 7.4), fixing 30 min in 2% HEPES-buffered paraformaldehyde, pH 7.4, rinsing three times in TBS and incubating the cells for 30 min in TBS, 0.1% BSA, 5% goat serum. Cells were incubated for 1 hr at room temperature with 5 µg/ml mAb 281-2 (specific for extracellular domain of syndecan-1 core protein) (M. Jalkanen, H. Nguyen, A. C. Rapraeger, N. Kurn, M. Bernfield, *J. Cell Biol.*, 101:976 (1985)) or non-specific rat $IgG_{2A}$ (Zymed, San Francisco, Calif.). Cells were then rinsed 3×5 min with TBS, incubated with alkaline phosphatase conjugated goat anti-rat antibody (Caltag, San Francisco, Calif.) for 30 min, rinsed 3×5 min with TBS, and alkaline phosphatase activity determined by measuring the absorbance at 405 nm of a 1 mg/ml solution of p-nitrophenolphosphate (Sigma, St. Louis, Mo.) in 10 mM Tris, 100 mM NaCl, 5 mM MgCl pH 9.5. Linear rates of absorbance change over time were determined by an automated microplate reader (Molecular Devices, Menlo Park, Calif.). Cells were then rinsed 3× with TBS and cellular protein determined by solubilizing cells in individual wells with 20 µl of 0.1N NaOH followed by protein determination (BCA protein assay, Pierce, Rockford, Ill.).

This assay was shown to measure the amount of cell surface syndecan-1 accurately by comparing it with results obtained by removing cell surface syndecan-1 quantitatively from cells in duplicate wells (20 µg/ml trypsin at 4° C. for 10 min), and measuring the released syndecan-1 by radioimmunoassay. These measurements correlated strongly over the range of syndecan-1 detected in this study (r=0.96), confirming that the ELISA assay provides a quantitative assessment of cell surface syndecan-1.

Wound fluid was collected in vinyl chambers (P.A. Medical Corp., Columbia, Tenn.) attached aseptically over 1.2 mm deep partial thickness wounds created on the skin of three to four month-old Yorkshire pigs. Each chamber received 1 ml of sterile 0.9% NaCl containing penicillin G and streptomycin as previously described (K. 1 Breuing, E. Eriksson, P. Liu, D. R. Miller, *J. Surg. Res.*, 52:50 (1992). At 24 hr intervals the fluid within the chamber was removed, passed through an 0.45 μm sterile filter and the chamber and saline solution replaced. Animal care was done in accordance with institutional guidelines.

Of a variety of biological fluids and growth factors, only porcine wound fluid collected during the early phase of wound repair (approximately the first six days), FGF-2, and PDGF-AB increased cell surface syndecan-1 (each approximately three to four-fold after 48 hr culture). Treatment with FGF-2 and PDGF-AB also increased cell number by about two-fold. However, a wound fluid preparation after passage through a heparin-sepharose column to remove heparin-binding factors such as PDGF, FGF-2 and HB-EGF, caused no detectable change in cell number, cell protein or morphology, but retained its syndecan-1 inductive activity. Therefore, an inductive activity not duplicated by several other biological fluids or growth factors was detected in the fluid released during wound repair.

EXAMPLE 2

Determination of effect of concentration and cell density on syndecan induction response to wound fluid Syndecan-1 induction in vivo is in condensed mesenchymal cells which show increased syndecan-1 mRNA levels and reduced syndecan-1 glycosylation (Bernfield, et al., (1992)). Thus, experiments were performed to evaluate the inductive response of cells to the wound fluid preparation.

FIGS. 1A and B demonstrate induction of syndecan-1 expression by wound fluid. FIG. 1A shows that induction of cell surface syndecan-1 is dependent on wound fluid concentration and cell density. Post-confluent (open squares) or 50% confluent (closed circles) NIH 3T3 cells were treated for 24 hours with culture medium (DMEM, Mediatech, Washington, D.C. with 4.5 gm/L glucose, 10% defined bovine serum, Hyclone, Logan, Utah, penicillin and streptomycin) containing the indicated concentrations (0.1 to 0.7 mg/ml) of wound fluid after passage through heparin-sepharose, then assayed for cell surface syndecan-1 by ELISA. Data are normalized for total cellular protein per well (7 μg/well for confluent and 4 μg/well for subconfluent cells) and represent the mean of triplicate determinations±SD of a single experiment representative of three experiments.

FIG. 1B shows that wound fluid stabilizes induced syndecan-1 at the cell surface. Post-confluent NIH 3T3 cells were cultured in medium as described above, containing the wound fluid preparation (400 μg protein/ml), for the time periods indicated and then assayed by ELISA. At 60 hours some wells (open squares) were rinsed once with medium and fresh medium without wound fluid added prior to assay. Data represent the mean of triplicate determinations±SD of a single experiment representative of two experiments.

FIGS. 2A and 2B demonstrate that wound fluid increases syndecan-1 and -4 transcript accumulation. Total RNA was extracted from post-confluent cultures of NIH 3T3 cells at zero, six, ten, 24 and 48 hrs after culture in medium containing the wound fluid preparation (400 μg protein/ml). Equal amounts of RNA, approximately 20 μg, were analyzed by separation on a 1% agarose formaldehyde gel, transfer to GeneScreen Plus™ membrane (DuPont-New England Nuclear), and hybridization to random primer labeled mouse syndecan-1 full-length cDNA or the 800 bp Pst I fragment of murine β-actin RNA at 65° C. in Quick Hyb™ Solution (Stratagene, La Jolla, Calif.) per manufacturer's instructions. Subsequent washing was in 2×SSPE, 0.1% SDS for 2×15 min at room temperature, and in 0.2×SSPE, 0.1% SDS, 2×15 min at 55° C. The membrane was then stripped and rehybridized with a murine β-actin probe. Autoradiograms were exposed for 8 h and 2 h for syndecan-1 and β-actin respectively.

The results show that syndecan-1 and -4 are induced within six to ten hours following exposure.

The results demonstrate that post-confluent NIH 3T3 cells responded in a dose-dependent manner, reaching maximal syndecan-1 induction at approximately 300 μg/ml of the crude wound fluid preparation (FIG. 1A). However, at 50% confluence, the cells expressed lower baseline levels of syndecan-1 and failed to be induced (FIG. 1A). This lack of response was also seen in subconfluent cells growth-arrested by either 12,500 rads gamma irradiation or treatment with mitomycin C. The kinetics of induction by the wound fluid preparation showed that cell surface syndecan-1 increased nearly linearly for 60 hours and then plateaued at approximately three-fold (FIG. 1B). Replacing the medium at 24 hour intervals with fresh medium containing the wound fluid preparation caused the same rate and extent of induction. However, when medium containing the wound fluid preparation was replaced with fresh medium alone, cell surface syndecan-1 was lost rapidly with a half-life of about 1.5 hours.

EXAMPLE 3

Selectivity of Response of Cell Surface Molecules to Wound Fluid Factor

The induction was accompanied by significant changes in syndecan-1 and syndecan-4 mRNA amount and core protein glycosylation, but also with minor changes in other cell surface and secreted proteins. Total RNA, the syndecan-1 extracellular domain released by trypsin, and proteins at the cell surface or secreted into the medium, were analyzed from cells treated with wound fluid. Northern blot analysis demonstrates an increase in both 2.6 and 3.4 kb syndecan-1 transcripts and 2.6 kb syndecan-4 as early as six hours after exposure to the wound fluid preparation, reaching a maximum of about 3.5-fold and 5 15-fold induction, respectively, after 24 hours. Syndecan-2 and syndecan-3 were not induced. No apparent differences were noted in proteins labeled by cell surface iodination with lactoperoxidase on 10% PAGE and differences only in bands at about 160,000 and about 35,000 Da were seen in conditioned media proteins following $^{35}$S-methionine labeling. These observations suggest that the response to induction by the wound fluid preparation is relatively selective when compared to the cellular response to mitogenic factors known to be present in untreated would fluid.

EXAMPLE 4

Selectivity of Wound Fluid Factor as to Cell Type

A variety of cell types were cultured to confluence and tested for induction of cell surface syndecan-1 by the wound fluid preparation. All post-confluent cells of mesenchymal origin tested, including five independently prepared cultures of primary mouse dermal and embryonic fibroblasts, NIH 3T3, Swiss 3T3, and C3H 10T1/2 fibroblasts, Balb/c 3T3 endothelioid cells, and capillary endothelial cells, responded to the wound fluid preparation with an increase in cell surface syndecan-1. On the other hand, all non-mesenchymal cells tested, including the cerebellar cell line C17 and a variety of epithelia, including NMuMG mammary, NMuLI hepatic, primary mouse keratinocyte, and keratinocyte cell lines (Balb MK, BK-1, PAM 212), failed to respond.

Therefore, wound fluid influenced multiple aspects of syndecan expression, including abundance and half-life at the cell surface, increased syndecan-1 mRNA, and decreased extent of glycosylation. These changes are similar to those of syndecan in mesenchymal cells during differentiation and embryonic tissue interactions. Furthermore, the time of appearance and mesenchymal cell selectivity of the inductive activity in wound fluid duplicate the induction of syndecan-1 observed in repairing wounds in vivo, as reported by Elenius, et al., (1991), indicating that the factor(s) responsible for induction in the in vitro system are also significant in vivo.

EXAMPLE 5

Purification of Syndecan-1 and -4 inductive Activity

To purify the syndecan-1 inductive activity, fluid pooled from day one to six wounds was partially purified by precipitation at pH 4.0, which removed 75% of total protein but less than 10% of the inductive activity.

Syndecan-1 inductive activity was then further purified by a combination of cation exchange chromatography and reversed phase HPLC. For cation exchange chromatography, the supernatant from an overnight 4° C. incubation of wound fluid at pH 4.0 was dialyzed to 20 mM Tris, 100 mM NaCl, pH 7.4, and applied to a 16×150 mm Toyopearl™ SP650S column (Tosohaas, Philadelphia, Pa.). After extensive washing with 0.2 M NaCl, activity was eluted with a linear NaCl gradient. Syndecan-1 inductive activity was determined as described above by 72 hr treatment with a 1/20 dilution of each fraction in culture medium.

Syndecan-1 inductive activity (fractions 13–15) from the cation exchange chromatography were applied to a C4 reversed phase column (4.6×250 mm Vydac, Hesperica, Calif.) and eluted with an acetonitrile gradient in 0.1% trifluoracetic acid. Eluted fractions (1 ml) were lyophilized, redissolved in 25 µl PBS, and syndecan-1 inductive activity determined as described above by 72 hrs treatment with a 1/30 dilution of each fraction in culture medium.

The activity appeared to be cationic as it was retained on a cation exchange column at 0.2 M NaCl and eluted at high salt concentrations in a broad peak between 0.65 and 0.8 M NaCl. The activity present in this fraction was abolished by both trypsin digestion (20 µg/ml, 37° C. for 30 min) and heat (56° C. for 30 min), suggesting that it was associated with protein.

Active fractions from the cation exchange chromatography (fractions 13–16) were adsorbed on a C4 reverse phase HPLC column equilibrated with 5% acetonitrile in 0.1% trifluoracetic acid and eluted in an acetonitrile gradient. The activity eluted reproducibly in two sharp peaks at 33% and 39% acetonitrile. These fractions represent a 700 to 1000-fold purification from crude wound fluid with a yield of 1 to 2% of the original activity.

This fraction was analyzed directly by PAGE, mass spectrometry, and amino acid sequencing. Both PAGE and mass spectroscopy were consistent with a highly purified peptide of mass about 4708 Da, indicating a peptide of about 39 amino acids. Sequencing established the N-terminal 36 amino acids unequivocally without detection of minor sequences, Seq. ID No. 1, Arg Arg Arg Pro Arg Pro Pro Tyr Leu Pro Arg Pro Arg Pro Pro Pro Phe Phe Pro Pro Arg Leu Pro Pro Arg Ile Pro Pro Gly Phe Pro Pro Arg Phe Pro Pro Arg Phe Pro. The sequence is identical with the N-terminal 36 amino acids of PR-39, a proline- and arginine-rich 39 amino acid peptide previously found in pig intestine, as described in PCT WO92/22578 by Lee, et al. Although known to have antibacterial activity, the peptide has not previously been associated with mesenchymal cells or interactions with eucaryotic cells.

EXAMPLE 6

Demonstration of syndecan-1 inducing activity of chemically synthesized PR-39

Figure 3A:
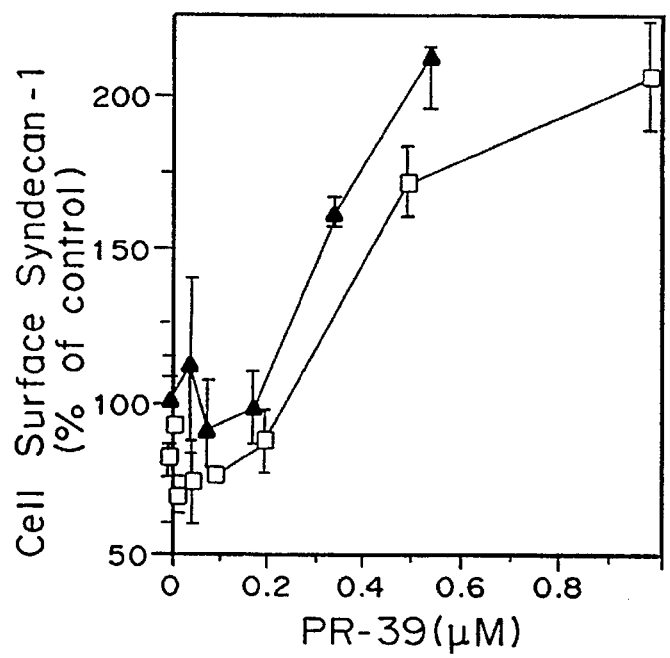
FIG. 3A is a graph of syndecan-1 (mOD/min) versus concentration of PR-39 (µM) showing that synthetic PR-39 induces syndecan-1 in a dose dependent manner. Data represent the mean of triplicate determinations±SD of a single experiment representative of two experiments.
Figure 3B:
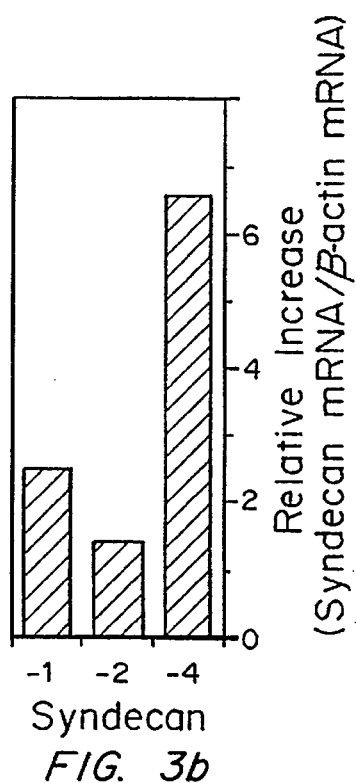
FIG. 3B is a graph of syndecan mRNA levels after culture of NIH-3T3 cells with synthetic PR-39 (1 µM) for 24 hours.

It was demonstrated that PR-39 possesses syndecan inductive activity by treating NIH-3T3 cells with media containing synthetically prepared PR-39, as shown by FIGS. 3A and 3B. PR-39 was synthesized by Chiron mimotopes peptide systems (San Diego, Calif.) and purity analysis performed by RP-HPLC and mass spectrometry. The peptide was found to be 96% pure by RP-HPLC with a molecular weight of 4721.1. The lyophilized powder was dissolved in 25% acetonitrile, 0.1% TFA, aliquoted for the indicated concentrations, lyophilized and reconstituted in culture media. Cells were exposed to PR-39 in culture medium for 43 hours prior to determination of cell surface syndecan-1 levels by ELISA. Open boxes represent synthetically prepared PR-39, closed triangles represent structurally derived and purified PR-39. Data represent the mean of triplicate determinations±SD of a single experiment representative of two experiments.

Cell surface syndecan-1 was induced by synthetic PR-39 in a concentration dependent manner, thereby demonstrating that syndecan-1 induction is due to PR-39 and not to undetected trace contaminants present in the preparation from wound fluid.

The results presented here demonstrate that an antibacterial peptide, PR-39, is in the fluid recovered from skin wounds and that it enhances the expression of cell surface syndecan-1 on mesenchymal cells. These findings are unexpected because such antimicrobial peptides were both not known to exist in the wound environment and not known to influence the selective expression of cell surface proteoglycans.

In mammals, other antimicrobial peptides have been shown to be weakly mitogenic and affect cell viability, ACTH-responsiveness, plasma membrane potential and promote wound healing. The finding of syndecan-1 induction by a peptide with antimicrobial activity suggests that membrane permeating peptides function as signaling molecules in complex cellular behaviors.

EXAMPLE 7

Uptake and binding characteristics of PR-39, Effect on Cell Permeability and Morphology The uptake and binding of PR-39 was demonstrated as follows. PR-39 was iodinated using the Iodogen procedure (Pierce T). The influx and efflux kinetics were calculated, accessable compartments were evaluated, and total uptake measured in NIH-3T3 cells.

Figure 4:
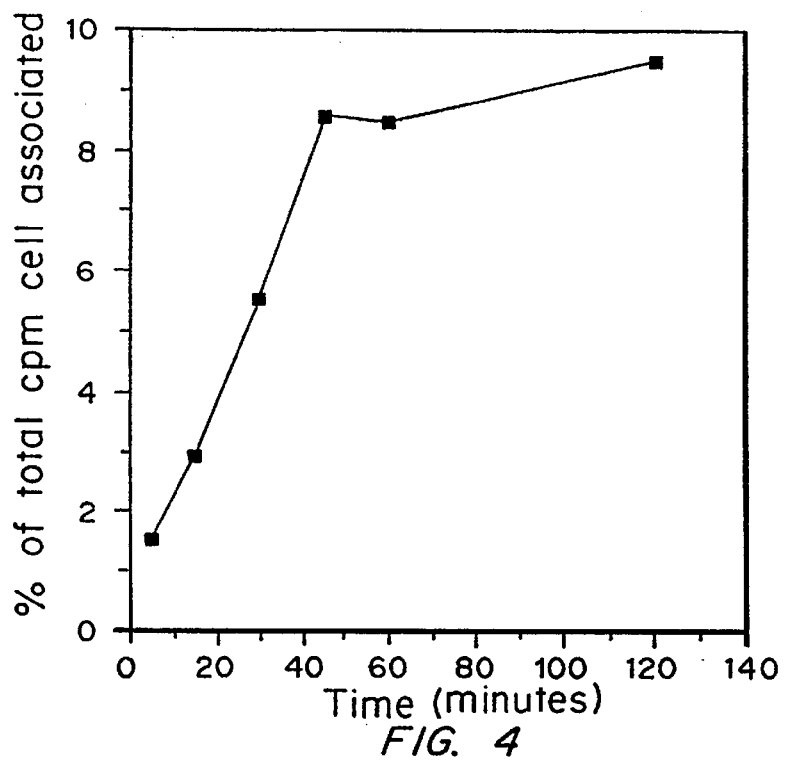
FIG. 4 is a graph showing uptake of PR-39 by NIH-3T3 cells. The percent of radioactive PR-39 (in cpm) specifically associated with the cells is plotted versus time of incubation until radioactive PR-39 (in minutes), showing that PR-39 is rapidly taken up by cells and reaches a saturation point.

The results are shown in FIG. 4 and show that the peptide, of a size not normally taken up by intact cells, rapidly associates with and enters NIH-3T3 cells.

Cell permeability after PR-39 treatment was then measured. NIH-3T3 cells were cultured to confluence on chamber slides. 0, 0.1, 0.5, 1, and 10 µM PR-39 was added to the culture medium and incubated 60 minutes at 37° C.; then 50 µg/ml propium iodide (FW 688) was added. A 2/20× field of fluorescent cells shown with PR-39, 100% (approximately 50/20×) with 0.1% Triton™ showed no large perability changes in the membrane.

To determine the effect on cell morphology, NIH-3T3 cells were cultured to confluence on coverslips in 24 well plates. 2 µM PR-39 was added the medium and cultured for 72 hr. 2% PFA and acetone were used to fix cells and cells were stained with f-actin with rhodamine phalloidin. No change in cell morphology was detected.

Modifications and variations of the methods and compositions described herein will be obvious to those skilled in the art from the foregoing detailed description and are intended to come within the scope of the appended claims.

We claim:

1. A method for modulating mesenchymal cell interactions comprising administering to the cells an mount of synducin effective to alter expression of a syndecan selected from the group consisting of syndecan-1 and syndecan-4 on the mesenchymal cells.

2. The method of claim 1 wherein the synducin specifically induces expression of syndecan-1.

3. The method of claim 1 wherein the synducin is PR-39.

4. A composition for modulating mesenchymal cell interactions comprising purified synducin in a pharmaceutical carrier for systemic administration at a concentration between 0.1 and 1.0 micromolar or for topical administration at a concentration between 0.2 and 5.0 micromolar.

5. The composition of claim 4 further comprising stabilizers of the synducin biological activity.

6. The composition of claim 4 formulated for systemic administration.

7. The composition of claim 4 wherein the peptides are stabilized to increase in vivo half-life.

8. The composition of claim 4 formulated in a polymeric delivery composition.

9. The method of claim 1 wherein the synducin specifically induces expression of syndecan-4.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 39 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( x ) PUBLICATION INFORMATION:
    ( A ) AUTHORS: Lee, Jong-Youn
      Boman, Hans G.
      Mutt, Viktor
      Jornvall, Hans
    ( B ) TITLE: Novel Polypeptides And Their Use
    ( C ) JOURNAL: PCT WO 92/22578
    ( G ) DATE: 12/23/92
    ( K ) RELEVANT RESIDUES IN SEQ ID NO:1: FROM 1 TO 39

( x i ) SEQUENCE DESCRIPTION: SEQ ID NO:1:

```
Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
            35
```